US009068970B2

(12) United States Patent
Hossler et al.

(10) Patent No.: US 9,068,970 B2
(45) Date of Patent: Jun. 30, 2015

(54) EFFICIENT AND EFFECTIVE SUPPLEMENT SCREENING FOR THE DEVELOPMENT OF CHEMICALLY DEFINED MEDIA IN CELL CULTURE

(75) Inventors: Patrick Hossler, Westborough, MA (US); Christopher Racicot, Auburn, MA (US); Sean McDermott, Warwick, RI (US); John C. Fann, Shrewsbury, MA (US)

(73) Assignee: Abbvie Inc., North Chicago, IL (US)

( * ) Notice: Subject to any disclaimer, the term of this patent is extended or adjusted under 35 U.S.C. 154(b) by 655 days.

(21) Appl. No.: 13/289,502

(22) Filed: Nov. 4, 2011

(65) Prior Publication Data

US 2012/0129727 A1 May 24, 2012

Related U.S. Application Data

(60) Provisional application No. 61/410,709, filed on Nov. 5, 2010.

(51) Int. Cl.
*C12N 5/00* (2006.01)
*C12N 5/02* (2006.01)
*C40B 30/06* (2006.01)
*G01N 33/50* (2006.01)
*C12Q 1/02* (2006.01)

(52) U.S. Cl.
CPC ............ *G01N 33/5008* (2013.01); *C12Q 1/025* (2013.01)

(58) Field of Classification Search
CPC .................. A61B 2562/0295; A61B 5/14532; A61B 5/14546; A61B 5/1455; C07K 16/303; C12Q 1/025; C12Q 1/04; C12Q 2304/20; C12Q 2304/22; C12Q 2304/24; G01N 2035/00148; G01N 21/274; G01N 21/314; G01N 21/35; G01N 2333/645; G01N 2333/72; G01N 27/3271; G01N 33/5008; G01N 33/57438; Y10S 435/81; Y10S 435/822; Y10S 435/911; Y10S 435/975
See application file for complete search history.

(56) References Cited

U.S. PATENT DOCUMENTS 6,727,076 B2 * 4/2004 Bochner ........................ 435/34
7,009,180 B2 * 3/2006 Sterling et al. ........... 250/339.12

OTHER PUBLICATIONS

International Search Report and Written Opinion for PCT.US2011/059263, dated Jul. 4, 2012 (corresponds to U.S. Appl. No. 13/289,502).

Kuchibhatla, et al., “A rapid and effective screening process of animal component free hydrolysates to increase cell performance”, *IBC bioprocess International Conference*, (Jan. 1, 2004), retrieved from the Internet: URL:http://www.bd.com/ds/technicalCenter/whitepapers/1r876.pdf, (retrieved on Jan. 18, 2012).

Lin, et al., “Development and application of an animal component free single-cell cloning medium for Chinese hamster ovary cell lines”, *Cell Technology For Cell Products*, Chapter VI:595-597 (Jan. 1, 2007).

Sanford, et al., “BIOT 236-High-throughout screening approach to identify media supplements that alter N-linked glycosylation distribution of monoclonal antibodies produced from CHO cells”, *Abstracts of Papers American Chemical Society*, 238:236-BIOT (2009).

Zhang, et al., “Rapdi development and optimization of cell culture media”, *Biopharm International 200801 US*, 21(1):60-68 (2008).

* cited by examiner

*Primary Examiner* — Chris R Tate
*Assistant Examiner* — Douglas F White
(74) *Attorney, Agent, or Firm* — Lathrop & Gage LLP; Andrew T. Wilkins, Esq.

(57) ABSTRACT

The present invention relates to methods of selecting and developing a chemically defined media (“CDM”) for use in the manufacture of biological products. In particular, the present invention is directed to screening methods to determine cell culture technique media supplement blends with enhanced performance characteristics. The present invention is also directed to identifying CDM supplement blends that demonstrate significant increases in harvest titer and/or viable cell density.

6 Claims, 5 Drawing Sheets

EFFICIENT AND EFFECTIVE SUPPLEMENT SCREENING FOR THE DEVELOPMENT OF CHEMICALLY DEFINED MEDIA IN CELL CULTURE

This application is claims the benefit of the priority date of U.S. Ser. No. 61/410,709, filed Nov. 5, 2010, which is hereby incorporated by reference in its entirety.

1. INTRODUCTION

The present invention relates to methods of selecting and developing a chemically defined media ("CDM") for use in the manufacture of biological products. In particular, the present invention is directed to screening methods to determine cell culture media supplement blends with enhanced performance characteristics. The present invention is also directed to identifying CDM supplement blends that demonstrate significant increases in harvest titer and/or viable cell density.

2. BACKGROUND OF THE INVENTION

The use of chemically defined media in mammalian cell culture techniques is advantageous for many reasons, including, but not limited to, better traceability of raw materials, and better lot-to-lot consistency, which facilitate consistency in process performance. In contrast, the use of undefined, complex media components, such as yeast and soy hydrolysates, contribute to process performance variability, including differences in cell growth, product titer, and product quality attributes. Accordingly, the development and refinement of chemically defined media is particularly important for upstream process development, particularly in light of regulatory concerns and the desire for process robustness.

CDM, even when completely defined, can have one hundred or more individual chemical species whose relative contributions towards process performance are not completely understood. Therefore, it is difficult to predict what effect will be observed for any given addition or removal of a supplement. Furthermore, obtaining information regarding the relative roles of supplements is difficult in bioreactor scale culture as only a handful of compounds can be tested simultaneously and the endeavor would be complicated, expensive, and time-consuming process.

In light of the foregoing, it would be desirable to have a streamlined and reliable screening method to screen supplements in a high-throughput format. The instant invention meets that need by introducing a compound-by-compound screening approach that provides a robust, scalable, and economical method for inclusion into future media development and refinement strategies.

3. SUMMARY OF THE INVENTION

The present invention relates to methods of improving and refining supplement blends for use in increasing cell culture performance across distinct chemically defined media and/or cell lines. In certain embodiments, the present invention relates to methods of efficiently screening and statistically analyzing media blends to identify those that induce high performance product production.

In accordance with the disclosed subject matter, methods are provided herein for the use of high-throughput screening platforms capable of screening media supplements that improve cell culture process performance. In certain embodiments, the disclosed subject matter provides improved cell culture processes comprising the steps of: selecting a plurality of supplements; statistically designing a plurality of different blends of supplements to test; screening the designed supplement blends in the context of a base chemically defined media; and statistically analyzing the blends to identify those that induce high performance product production.

4. BRIEF DESCRIPTION OF THE FIGURES

FIG. 1 depicts a scatter plot of the process performance results of the supplement screening experiments. Specifically, FIG. 1 depicts a scatter plot with four quadrants representing the differences in cell culture performance based on whether supplement blends increase or decrease titer and VCD relative to the average of the unsupplemented control (top left-Titer ↑, VCD ↓; top right-Titer ↑, VCD ↑; bottom left-Titer ↓, VCD ↓; and bottom right-Titer ↓, VCD ↑).

FIG. 2 depicts the dispersal of the effects of varying concentrations of polyamines, cupric sulfate, essential amino acids pooled together (EAA), and potassium phosphate.

FIG. 3 depicts the effects of zinc chloride combined with folate and calcium pantothenate combined with EAA.

5. DETAILED DESCRIPTION OF THE INVENTION

Figure 1:
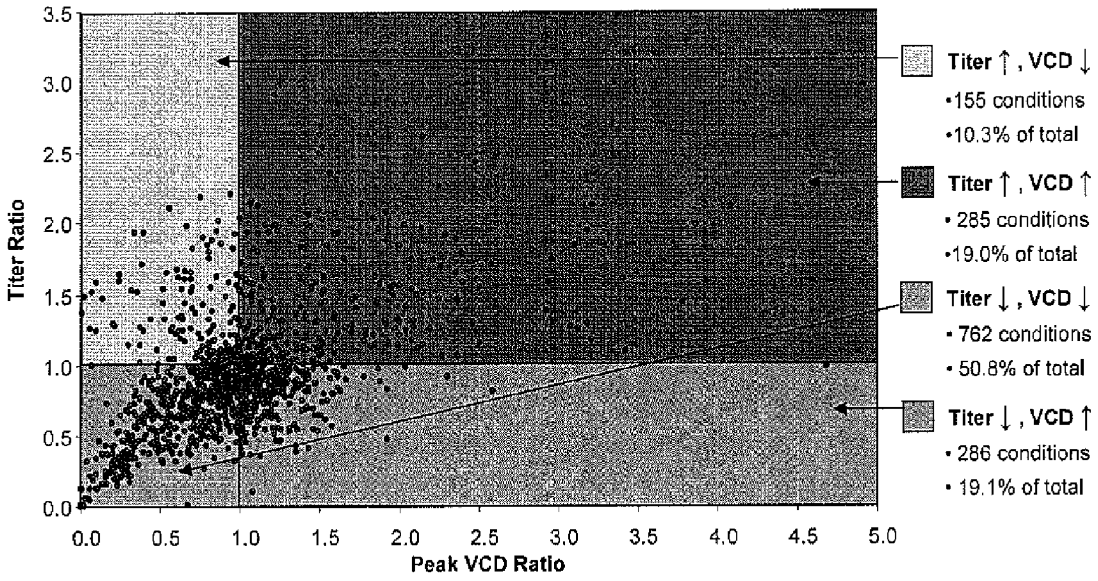

The present invention relates, in certain embodiments, to methods of improving and refining supplement blends for use in increasing cell culture performance across distinct chemically defined media and/or cell lines. For example, in certain embodiments, the present invention relates to methods of efficiently screening and statistically analyzing media blends to identify those that induce high performance product production.

In accordance with the disclosed subject matter, methods are provided herein for the use of high-throughput screening platforms capable of screening media supplements that improve cell culture process performance. In certain embodiments, the disclosed subject matter provides improved cell culture processes comprising the steps of: selecting a plurality of supplements; statistically designing a plurality of different blends of supplements to test; screening the designed supplement blends in the context of a base chemically defined media; and statistically analyzing the blends to identify those that induce high performance product production.

5.0. DEFINITIONS

As used in the specification and the appended claims, the singular forms "a," "an" and "the" include plural referents unless the context clearly dictates otherwise. Thus, for example, reference to "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, or within 5-fold, or within 2-fold, of a value.

The term "supplement" as used herein is any compound or other material, whether chemical or biological in origin, which may be used in a media for cell culture to maintain and/or promote the growth and/or differentiation of cells. Non-limiting examples of supplements include amino acids, salts, metals, sugars, lipids, nucleic acids, hormones, vitamins, fatty acids, proteins, enzymes, nucleosides, metabolites, surfactants, emulsifiers, inorganic salts, and polymers. In certain embodiments, the supplement is selected from the group comprised of L-arginine; Palmitic acid; $CuSO_4*5H_2O$; L-alanine; L-histidine*HCl*$H_2O$; Stearic acid; $ZnSO_4*7H_2O$; L-asparagine; L-leucine; Cholesterol; Selenite*2Na; L-aspartic acid; L-cystine; Arachidonic acid; Ferric citrate; L-glutamic acid; L-lysinea; Tween-80; $MnSO_4*H_2O$; L-proline; L-methionine; Linolenic acid; $Na_2SiO_3*9H_2O$; L-serine; L-phenylalanine; Tocopherol acetate; Molybdic acid, ammonium salt; L-glycine; L-threonine; Pluronic F-68; $NH_4VO_3$; Galactose; L-valine; Arachidonic acid; $NiSO_4*6H_2O$; Sucrose; L-tryptophan; Linoleic acid; $SnCl_2$ (anhydrous); Sodium pyruvate; L-isoleucine; Oleic acid; AlCl3*6$H_2O$; Inosine; L-tyrosine; Myristic acid; $AgNO_3$; Xanthine; choline chloride; Maltose; $Ba(C_2H_3O_2)2$; Adenosine; D-calcium pantothenate; Para-amino benzoic acid (PABA); KBr; Guanosine; Folic acid; Potassium phosphate; $CdCl_2$; Uridine; Nicotinamide; Calcium pantothenate; $CoCl_2*6H_2O$; Cytidine; Pyridoxal hydrochloride; EDTA; $CrCl_3$; NADH; Cupric sulfate; NaFe; NADPH; Thiamine hydrochloride; Riboflavin; $GeO_2$; Putrescine; i-inositol; α-cyclodextrin; KI; Spermine, free base; Xylose; Biotin; RbCl; Spermidine, free base; N-acetylglucosamine; β-cyclodextrin; $ZrOCl_2*8H_2O$; Hypoxanthine; Choline chloride; Thymidine; L-alanyl-L-glutamine; Folate; Iron supplement; Concanavalin A; Pyridoxine hydrochloride (vitamin B-6); Manganese chloride; Taurine; Ethanolamine; Zinc chloride; Fructose; Hydrocortisone; Sodium citrate; Mannose; N-acetylgalactosamine; Sarcosine; Cyanocobalamin (vitamin B-12); Glutathione, reduced; Cellastim™; and Lacromin™

The term "supplement blend" as used herein refers to two or more combinations of supplements in any concentration. In particular embodiments, the supplement blends contain two or more supplements listed in Table 1, below.

TABLE 1

Examples of Supplements

| | | | |
|---|---|---|---|
| L-arginine[a] | Palmitic acid[d] | $CuSO_4*5H_20$[e] | L-alanine[b] |
| L-histidine*HCl*$H_20$[a] | Stearic acid[d] | $ZnSO_4*7H_20$[e] | L-asparagine[b] |
| L-leucine[a] | Cholesterol[d] | Selenite*2Na[e] | L-aspartic acid[b] |
| L-cystine | Arachidonic acid[d] | Ferric citrate[e] | L-glutamic acid[b] |
| L-lysine[a] | Tween-80[d] | $MnSO_4*H_20$[e] | L-proline[b] |
| L-methionine[a] | Linolenic acid[d] | $Na_2SiO_3*9H_20$[e] | L-serine[b] |
| L-phenylalanine[a] | Tocopherol acetate[d] | Molybdic acid, ammonium salt[e] | L-glycine[b] |
| L-threonine[a] | Pluronic F-68[d] | $NH_4VO_3$[e] | Galactose[j] |
| L-valine[a] | Arachidonic acid[d] | $NiSO_4*6H_20$[e] | Sucrose[j] |
| L-tryptophan[a] | Linoleic acid[d] | $SnCl_2$ (anhydrous)[e] | Sodium pyruvate[j] |
| L-isoleucine[a] | Oleic acid[d] | $AlCl_3*6H_20$[e] | Inosine[k] |
| L-tyrosine[a] | Myristic acid[d] | $AgNO_3$[e] | Xanthine[k] |
| choline chloride[c] | Maltose | $Ba(C_2H_3O_2)_2$[e] | Adenosine[k] |
| D-calcium pantothenate[c] | Para-amino benzoic acid (PABA) | KBr[e] | Guanosine[k] |
| Folic acid[c] | Potassium phosphate | $CdCl_2$[e] | Uridine[k] |
| Nicotinamide[c] | Calcium pantothenate | $CoCl_2*6H_20$[e] | Cytidine[k] |
| Pyridoxal hydrochloride[c] | EDTA | $CrCl_3$[e] | NADH |
| Riboflavin[c] | Cupric sulfate | NaF[e] | NADPH |
| Thiamine hydrochloride[c] | Riboflavin | $GeO_2$[e] | Putrescine[f,i] |
| i-inositol[c] | α-cyclodextrin | KI[e] | Spermine, free base[f] |
| Xylose | Biotin | RbCl[e] | Spermidine, free base[f] |
| N-acetylglucosamine | β-cyclodextrin | $ZrOCl_2*8H_20$[e] | Hypoxanthine[f] |
| Choline chloride | Thymidine | L-alanyl-L-glutamine | Folate |
| Iron supplement[g] | Concanavalin A | Pyridoxine hydrochloride (vitamin B-6) | i-inositol |
| Manganese chloride | Taurine | Ethanolamine | Zinc chloride |
| Fructose | Hydrocortisone | Sodium citrate | Mannose |
| N-acetylgalactosamine | Sarcosine | Cyanocobalamin (vitamin B-12) | |
| Cellastim[TM,h] | Lacromin[TM,h] | | |

[a]Evaluated as part of a mixture (EAA)
[b]Evaluated as part of a mixture (NEAA)
[c]Denotes a component of the vitamin mixture evaluated (USBiological, Catalog # M3884)
[d]Denotes a component of the lipid mixture evaluated (Sigma-Aldrich, Catalog # L-0288)
[e]Denotes a component of the trace metal (TM) mixtures evaluated (Media Tech, Catalog #'s 99-182-CI, 99-175-CI, 99-176-CI)
[f]Denotes a component of the polyamines mixture evaluated (Sigma-Aldrich, Catalog # P8483)
[g]Commercially available mixture (Sigma-Aldrich, catalog #: I3153-10ML)
[h]Commercially available supplements (Invitria, Catalog # 777LAC015, 777HSA017)
[i]Denotes a compound in one of the evaluated mixtures that was also screened while not in a mixture
[j]Evaluated as part of a mixture
[k]Evaluated as part of a mixture The terms "media" or "basal media" as use herein refer to a nutritive composition that aids in sustaining, propagating, and/or differentiating cells. The terms "chemically defined media," "chemically defined basal media," and "CDM" as used herein refer to a media in which all of the components can be described in terms of their chemical formulas and are present in known concentrations. The terms "base chemically defined media" and "base CDM" as used herein refer to a preselected CDM which has not been developed by use of the method of the present invention. The term "high performance CDM" as used herein refers to a combination of base CDM and a supplement blend with one or more desired performance parameters.

The term "cells" as used herein refers to a cell population. The cells may be wild-type or recombinant. The terms "cell culture" or "cell culture technique" or "cell culture process" as used herein refer to methods and conditions suitable to survival and/or growth and/or differentiation of the cells.

5.1. Cells and Cell Culture Techniques

In certain embodiments, the cells of the present invention are prokaryote, yeast, or higher eukaryote cells. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In certain embodiments, the cells are eukaryotic microbes such as filamentous fungi or yeast. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwarmiomyces occidentalis*; and filamentous fungi such as, e.g., *Neurospora, Penicillium, Tolypocladium*, and *Aspergillus* hosts such as *A. nidulans* and *A. niger.*

In certain embodiments the cells are derived from multicellular organisms. In particular embodiments, the cells are invertebrate cells from plant and insect cells. Non-limiting examples include cells derived from *Spodoptera frugiperda* (caterpillar), *Aedes aegypti* (mosquito), *Aedes albopictus* (mosquito), *Drosophila melanogaster* (fruitfly), *Bombyx mori*, cotton, corn, potato, soybean, petunia, tomato, and tobacco can also be utilized.

In certain embodiments the cells are mammalian cells. In certain embodiments, the cells are Chinese Hamster Ovary (CHO cells) (including dhfr− CHO cells, described in Urlaub and Chasim, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. Other non-limiting examples of mammalian cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

In particular embodiments, the cells are transformed with expression or cloning vectors for producing products or portions thereof and cultured as appropriate for inducing promoters, selecting transformants, or amplifying the genes encoding the desired sequences. In a particular embodiment, standard molecular biology techniques are used to prepare the recombinant expression vector, transfect the cells, select for transformants, culture the cells and recover the product from the culture medium.

The cell culture techniques of the present invention can be practiced in any suitable culture vessel. For example, in certain embodiments, a culture vessel can refer to a glass, plastic, metal or other container that provides an environment for culturing cells. Non-limiting examples of such culture vessels include incubation vessels, microtiter plates, capillaries, and multi-well plates. In particular embodiments, the culture vessel is a multi-well plate.

The cells of the present invention can be cultured under suitable conditions for suitable periods of time, conditions that depend on the on the type(s) of cells being cultured and the product being produced. In certain embodiments, the cells are cultured for about two to about fourteen days. In certain embodiments, the cells are cultured from about four to about ten days.

In particular embodiments, the cells containing supplement blends are assayed for their ability to alter the production, transcription, translation, post-translational processing, intracellular transport, secretion, and/or turnover of one or more biological and chemical products in cells. Non-limiting examples of biological and chemical products include antibodies, proteins, antigens, toxins, hormones, growth factors, cytokines, clotting factors, enzymes, antibiotics, steroids, carbohydrates, lipids, nucleic acids, and fragments thereof.

The purity of the biological and chemical products may be analyzed using methods well known to those skilled in the art. None-limiting examples include size-exclusion chromatography, oligosaccharide analysis, Poros™ A HPLC assay, ELISA, western blot analysis, competitive binding assays, direct and indirect sandwich assays, and immunoprecipitation assays.

5.2. Assay of Supplement Blends

In certain embodiments of the present invention, the cell culture techniques are carried out using base CDM and one or more supplements or supplement combinations in a culture vessel. In certain embodiments, the cells, base CDM, and supplement or supplement combinations can be added in any order. In certain embodiments, the base CDM and supplement combinations are added to a culture vessel and the cells are then inoculated into the culture vessel. In particular embodiments, the vessels contain the same cells and base CDM while the supplement blend is different for each vessel. In another embodiment, multiple vessels contain the same cell, media, and supplement blend. In particular embodiments, multiple vessels contain the same supplement blend at different concentrations. In certain embodiments, two to six different concentrations of each supplement blend are tested. In particular embodiments, three different concentrations of each blend are tested.

The methods of the present invention can include cell culture processes that occur under a variety of environmental conditions. For example, but not by way of limitation, the cells employed in the methods of the instant invention may be cultured while stationary or while shaken. The cells may be cultured while stationary or while shaken. In certain embodiments, the cells are shaken at 210 rpm. In certain embodiments, the cells are cultured at a temperature between about 20° C. and about 45° C. In certain embodiments, the cells are cultured at a temperature between about 33° C. and about 37° C. In certain embodiments, the cells are cultured at a temperature between about 34° C. and about 35° C. In certain embodiments, the cells are cultured under ambient conditions. In certain embodiments, the cells are cultured in a humidified $CO_2$ incubator. In certain embodiments, the cells are cultured in a 5% humidified $CO_2$ incubator. In certain embodiments, the cell culture technique includes providing a barrier between the cells and ambient conditions. In certain embodiments, the barrier is sterile. In certain embodiments, the barrier is a gas permeable, sterile vessel cover. In certain embodiments, the total volume of the combinations of cells, base CDM, and supplements is from about 0.5 mL to about 2 L. In certain embodiments, the total volume is from about 1 mL to about 500 mL.

In particular embodiments, the cell culture technique is carried out by preparing cells with base CDM and various supplement combinations in a culture vessel. The cells, base CDM, and supplement combinations may be added in any order. In particular embodiments, the base CDM and supplement combinations are added to a culture vessel and the cells are then inoculated into the culture vessel. In particular embodiments, the vessels contain the same cells and base CDM while the supplement blend is different for each vessel. In another embodiment, multiple vessels contain the same cells, media, and supplement blend. In another embodiment, different cell cultures and/or base CDM may be used.

In certain embodiments, the cells are cultured for about one day to about two weeks prior to being assayed. In particular embodiments, the cells are cultured for about four to eight days prior to being assayed. In particular embodiments, each assay is carried out between two and six times on each combination of cells, media, and supplement blend. In a particular embodiment, the assays are carried out three times on each combination. In particular embodiments, the length of time between assays is about 12 to about 48 hours. In a certain embodiment, the length of time between assays is about 24 hours.

The cells are assayed for selected performance parameters. Non-limiting examples of performance parameters are harvest titer, viable cell density, pH, metabolite profile, and dissolved oxygen. In a certain embodiment, the performance parameters are viable cell density ("VCD") and harvest titer.

The assays for determining supplement performance may be carried out by any technique known in the art, including but not limited to spectrophotometrically, chromatographically, staining and visual observation, turbidity measurements, colorimetry, and/or measurement of optical density, bioluminescence, carbon dioxide, oxygen or ATP production, or consumption. Assays may be carried out using any known device, including but not limited to a spectrophotometer, chromatograph, fluorometer, flow cytometer, scintillation or gamma counter, automated cell counter, automated plate counter, or manual plate counter. In certain embodiments, commercially available assay kits such as the CellTiter 96 AQueous Solution Cell Proliferation Assay Kits™ (Promega, Madison, Wis.) are Used to Assay the performance parameters. In certain embodiments, the automated cell counter is a Cedex automated cell counter (Hoffman-La Roche, Basel, Switzerland). In certain embodiments, assays are performed via high performance liquid chromatography (HPLC). In certain embodiments, an affinity column is used. In particular embodiments, the affinity column is a Poros A™ affinity column (Applied Biosystems, Foster City, Calif.).

The steps of preparing mixtures of cells, media, and supplements blends and assaying may be repeated multiple times. In a certain embodiments the steps are repeated so that about five hundred to about two thousand mixtures, each containing a unique supplement blend, are assayed. In a certain embodiment, the steps are repeated so that at least one thousand mixtures are assayed. In particular embodiments, the assays are carried out concurrently. Alternatively or in addition, the assays may be carried out separately over any length of time. In certain embodiments, the assays are carried out over a period of about two to about twenty weeks.

The cell culture technique assays may be analyzed using any technique known in the art, including but not limited to fractional factorial design, univariate analysis, and/or multivariate analysis. In particular embodiments, Standard Analysis of Variance (ANOVA) is used to measure the significance of individual supplements and their respective interactions towards the resulting cell culture technique performance. Beneficial supplements may be identified through various methods or combinations thereof. One non-limiting example of a method of identifying a high performance blend is to use a relatively low p-value ($<0.10$) using ANOVA analysis. Another non-limiting example is an inspectional analysis to identify a positive trend in process performance as a result of a supplement. In yet another non-limiting example, an optimization subroutine intrinsic to statistics software can be used. It is important to note that the identification method is a mathematical exercise which can lead to multiple blends being identified as having the desired performance parameters, and the results highly dependent on the initial first guess in designing the statistical model to be used.

In certain embodiments, software is used to prepare statistical screening designs prior to initiating the assay. In a particular embodiment, the statistical designs are prepared using JMP7 commercially available statistics software (Cary, N.C.) with custom parameters options. In certain embodiments, the screening design is then followed to prepare mixtures of cells, base CDM, and supplements. These mixtures are then assayed and the results are analyzed.

In certain embodiments, a subset of the supplements identified as having better performance parameters can be selected for further testing. This subset of supplements may then be combined into any number of supplement blends, assayed, and analyzed as described above. In particular embodiments, the process of selecting a subset of supplements, assaying cells containing a base CDM and supplement blends, and then analyzing the results may be repeated one or more times. In certain embodiments, the supplement blends can be tested in various cells and/or base CDM.

5.3. High Performance Supplemental Blends

In certain embodiments, the present invention is directed to particular high performance supplemental blends. In certain embodiments, the supplemental blend comprises two or more supplements selected from the group comprised of: L-arginine; Palmitic acid; $CuSO_4*5H_2O$; L-alanine; L-histidine*HCl*$H_2O$; Stearic acid; $ZnSO_4*7H_2O$; L-asparagine; L-leucine; Cholesterol; Selenite*2Na; L-aspartic acid; L-cystine; Arachidonic acid; Ferric citrate; L-glutamic acid; L-lysinea; Tween-80; $MnSO_4*H_2O$; L-proline; L-methionine; Linolenic acid; $Na_2SiO_3*9H_2O$; L-serine; L-phenylalanine; Tocopherol acetate; Molybdic acid, ammonium salt; L-glycine; L-threonine; Pluronic F-68; $NH_4VO_3$; Galactose; L-valine; Arachidonic acid; $NiSO_4*6H_2O$; Sucrose; L-tryptophan; Linoleic acid; $SnCl_2$ (anhydrous); Sodium pyruvate; L-isoleucine; Oleic acid; $AlCl_3*6H_2O$; Inosine; L-tyrosine; Myristic acid; $AgNO_3$; Xanthine; choline chloride; Maltose; $Ba(C_2H_3O_2)_2$; Adenosine; D-calcium pantothenate; Para-amino benzoic acid (PABA); KBr; Guanosine; Folic acid; Potassium phosphate; $CdCl_2$; Uridine; Nicotinamide; Calcium pantothenate; $CoCl_2*6H_2O$; Cytidine; Pyridoxal hydrochloride; EDTA; $CrCl_3$; NADH; Cupric sulfate; NaFe; NADPH; Thiamine hydrochloride; Riboflavin; $GeO_2$; Putrescine; i-inositol; α-cyclodextrin; KI; Spermine, free base; Xylose; Biotin; RbCl; Spermidine, free base; N-acetylglucosamine; β-cyclodextrin; $ZrOCl_2*8H_2O$; Hypoxanthine; Choline chloride; Thymidine; L-alanyl-L-glutamine; Folate; Iron supplement; Concanavalin A; Pyridoxine hydrochloride (vitamin B-6); Manganese chloride; Taurine; Ethanolamine; Zinc chloride; Fructose; Hydrocortisone; Sodium citrate; Mannose; N-acetylgalactosamine; Sarcosine; Cyanocobalamin (vitamin B-12); Glutathione, reduced; Cellastim™; and Lacromin™. In certain embodiments, the supplemental blend comprises two or more supplements selected from the group comprised of: Polyamines mixture (Sigma-Aldrich, Catalog # P8483); Xylose; Mannose; Essential amino acid mixture (EAA—see Table 1); Choline chloride; Ethanolamine; Maltose; Manganese chloride; Vitamins mixture (USBiological, Catalog # M3884); Calcium pantothenate; Potassium phosphate; Linoleic acid; Cupric sulfate; Thymidine; EDTA; α-cyclodextrin; i-inositol; Hydrocortisone; β-cyclodextrin; Zinc chloride; L-alanyl-L-glutamine; Folate; and Pyridoxine hydrochloride. In certain embodiments, the concentration of the supplement, or supplements, present in the high performance supplemental blend is within the target range identified for the particular supplement, or supplements, outlined in Table 7 of Example 6.8. For example, but not by way of limitation, the supplement, or supplements, will be present in the high performance supplemental blend in the target range(s) outlined in Table 7 of Example 6.8 to achieve increased VCD, increased Harvest Titer, or both In certain embodiments, the supplemental blend will include: L-isoleucine; L-leucine; L-lysine; L-methionine; L-phenylalanine; L-threonine; L-tyrosine; L-valine; L-arginine; L-histidine*HCl*$H_2O$; L-tryptophan; Calcium pantothenate; Cupric sulfate; α-cyclodextrin; β-cyclodextrin; Folate; Manganese chloride; Potassium phosphate; Thymidine; i-inositol; and Zinc chloride. In certain embodiments the concentrations of the preceding supplements will be within the target ranges outlined in Table 7 of Example 6.8 to achieve increased VCD.

In certain embodiments, the supplemental blend will include: Putrescine Spermine, free base; Spermidine, free base; Hypoxanthine; L-isoleucine; L-leucine; L-lysine; L-methionine; L-phenylalanine; L-threonine; L-tyrosine; L-valine; L-arginine; L-histidine*HCl*$H_2O$; L-tryptophan; Maltose; Xylose, Choline chloride; Manganese chloride; Potassium phosphate; i-inositol; and Zinc chloride. In certain embodiments the concentrations of the preceding supplements will be within the target ranges outlined in Table 7 of Example 6.8 to achieve increased harvest titer.

In certain embodiments, the supplemental blend will include: Putrescine Spermine, free base; Spermidine, free base; Hypoxanthine; L-isoleucine; L-leucine; L-lysine; L-methionine; L-phenylalanine; L-threonine; L-tyrosine; L-valine; L-arginine; L-histidine*HCl*$H_2O$; L-tryptophan; Maltose; Xylose, Choline chloride; Potassium phosphate; i-inositol; and Zinc chloride. In certain embodiments the concentrations of the preceding supplements will be within the target ranges outlined in Table 7 of Example 6.8 to achieve both increased VCD and increased harvest titer.

6. EXAMPLES

6.1 Supplement Screenings 24-well plates were utilized at a working volume of 1.5 mL per well to serve as the platform for media supplement screening. An in-house, base chemically defined media (CDM #1) was used as the basal media for the purposes of the experiments. A recombinant IgG producing Chinese Hamster Ovary cell line (CHO cell line #1) was used for the media supplement screening phase of the experiments.

All 24-well plate screening experiments were designed using JMP7 commercially available statistics software (Cary, N.C.) using custom experimental options. Six individual media supplement screening experiments were performed to test over a hundred different supplements in statistically designed experiments and in a serial fashion. All screening experiments were performed at 345-35° C. cultured at 210 rpm on a shaker table in a 5% humidified $CO_2$ incubator. Gas permeable, rayon film plate covers (VWR International, Radnor, Pa., Catalog #60941-086) were employed as necessary to provide a sterile barrier between the well plates, the plastic plate cover, and the culture atmosphere. Supplement solutions were manually pipetted into the respective plate wells using concentrated, sterile stock solutions. The comprehensive list of media supplements evaluated for cell culture process improvement is shown below in Table 2:

TABLE 2

| List of Screened Supplements | | | |
|---|---|---|---|
| L-arginine[a] | Palmitic acid[d] | $CuSO_4*5H_20$[e] | L-alanine[b] |
| L-histidine*HCl*$H_20$[a] | Stearic acid[d] | $ZnSO_4*7H_20$[e] | L-asparagine[b] |
| L-leucine[a] | Cholesterol[d] | Selenite*2Na[e] | L-aspartic acid[b] |
| L-cystine | Arachidonic acid[d] | Ferric citrate[e] | L-glutamic acid[b] |
| L-lysine[a] | Tween-80[d] | $MnSO_4*H_20$[e] | L-proline[b] |
| L-methionine[a] | Linolenic acid[d] | $Na_2SiO_3*9H_20$[e] | L-serine[b] |
| L-phenylalanine[a] | Tocopherol acetate[d] | Molybdic acid, ammonium salt[e] | L-glycine[b] |
| L-threonine[a] | Pluronic F-68[d] | $NH_4VO_3$[e] | Galactose[j] |
| L-valine[a] | Arachidonic acid[d] | $NiSO_4*6H_20$[e] | Sucrose[j] |
| L-tryptophan[a] | Linoleic acid[d] | $SnCl_2$ (anhydrous)[e] | Sodium pyruvate[j] |
| L-isoleucine[a] | Oleic acid[d] | $AlCl_3*6H_20$[e] | Inosine[k] |

TABLE 2-continued

List of Screened Supplements

| | | | |
|---|---|---|---|
| L-tyrosine[a] | Myristic acid[d] | $AgNO_3$[e] | Xanthine[k] |
| choline chloride[c] | Maltose | $Ba(C_2H_3O_2)_2$[e] | Adenosine[k] |
| D-calcium pantothenate[c] | Para-amino benzoic acid (PABA) | KBr[e] | Guanosine[k] |
| Folic acid[c] | Potassium phosphate | $CdCl_2$[e] | Uridine[k] |
| Nicotinamide[c] | Calcium pantothenate | $CoCl_2*6H_20$[e] | Cytidine[k] |
| Pyridoxal hydrochloride[c] | EDTA | $CrCl_3$[e] | NADH |
| Riboflavin[c] | Cupric sulfate | NaF[e] | NADPH |
| Thiamine hydrochloride[c] | Riboflavin | $GeO_2$[e] | Putrescine[f,i] |
| i-inositol[c] | α-cyclodextrin | KI[e] | Sperrmine, free base[f] |
| Xylose | Biotin | RbCl[e] | Spermidine, free base[f] |
| N-acetylglucosamine | β-cyclodextrin | $ZrOCl_2*8H_20$[e] | Hypoxanthine[f] |
| Choline chloride | Thymidine | L-alanyl-L-glutamine | Folate |
| Iron supplement[g] | Concanavalin A | Pyridoxine hydrochloride (vitamin B-6) | i-inositol |
| Manganese chloride | Taurine | Ethanolamine | Zinc chloride |
| Fructose | Hydrocortisone | Sodium citrate | Mannose |
| N-acetylgalactosamine | Sarcosine | Cyanocobalamin (vitamin B-12) | Glutathione, reduced |
| Cellastim[TM,h] | Lacromin[TM,h] | | |

[a]Evaluated as part of a mixture (EAA)
[b]Evaluated as part of a mixture (NEAA)
[c]Denotes a component of the vitamin mixture evaluated (USBiological, Catalog # M3884)
[d]Denotes a component of the lipid mixture evaluated (Sigma-Aldrich, Catalog # L-0288)
[e]Denotes a component of the trace metal (TM) mixtures evaluated (Media Tech, Catalog #'s 99-182-CI, 99-175-CI, 99-176-CI)
[f]Denotes a component of the polyamines mixture evaluated (Sigma-Aldrich, Catalog # P8483)
[g]Commercially available mixture (Sigma-Aldrich, catalog #: 13153-10ML)
[h]Commercially available supplements (Invitria, Catalog # 777LAC015, 777HSA017)
[i]Denotes a compound in one of the evaluated mixtures that was also screened while not in a mixture
[j]Evaluated as part of a mixture
[k]Evaluated as part of a mixture Two cell culture performance indicators were measured in the high-throughput screening experiments: peak viable cell density and harvest titer. Time point samples were withdrawn from each of the respective plate wells on Days 6, 7, and 8 post inoculation and measured for their respective viable cell densities spectrophotometrically via the CellTiter 96 AQueous Solution Cell Proliferation Assay Kits™ (Promega, Madison, Wis.). Harvest Titer measurements were conducted via high performance liquid chromatography (HPLC) with a Poros A™ affinity column (Applied Biosystems, Foster City, Calif.). All experimental wells supplemented with a particular combination of media compounds were compared to an unsupplemented control, with the results expressed as relative values relative to the control. The highest increase in peak VCD was 392% and the highest increase in harvest titer was 205%.

6.2. Cell Culture Performance Indicators

Two cell culture performance indicators were measured in the high-throughput screening experiments as well as media verification experiments; peak viable cell density (VCD) and harvest titer. During screening, timepoint samples were withdrawn from each of the respective plate wells on Days 6, 7, and 8 post inoculation and measured for their respective viable cell densities (VCD) spectrophotometrically via the CellTiter 96 AQueous Solution Cell Proliferation Assay Kits™ (Promega, Madison, Wis.) Following a Method Adapted from the manufacturer's suggested procedure. A few days after the last cell count measurement sample the plates were centrifuged and the supernatant was collected and stored at −80° C. for future analysis. Harvest titer measurements were conducted via high performance liquid chromatography (HPLC) with a Poros A™ affinity column (Applied Biosystems, Foster City, Calif.). All experimental wells supplemented with a particular combination of media compounds were compared to an unsupplemented control, with the results expressed as values relative to the control. For the media verification experiments in larger-scale shaker and spinner flasks, viable cell density and viability were measured via Cedex automated cell counters (Roche Applied Science, Indianapolis, Ind.). Harvest titer measurements were similarly measured via HPLC.

6.3. Statistical Analysis of Supplement Screenings

Standard Analysis of Variance (ANOVA) was used to measure the significance of individual supplements and their respective interactions towards the resulting cell culture technique performance. Individual analyses were conducted on both peak viable cell density and harvest titer for each of the respective screening experiments. Three different levels of each media supplement were used in these experiments: unsupplemented (Level 1), lightly supplemented (Level 2), and heavily supplemented (Level 3). Beneficial compounds were identified by a relatively low p-value (<0.10), an inspectional analysis indicating a positive trend in process performance as a result of the supplement, or using both methods. The optimization subroutine intrinsic to the statistics software was used to analyze the screening dataset determine the identity of a high performance media blend. It is important to note that the selection method is a mathematical exercise which can lead to multiple blends identified as having the highest performance parameters, and the results are highly dependent on the initial first guess. Three particular high performance blends were identified for further evaluation: Blend 1 for facilitating higher growth, Blend 2 for facilitating higher titer, and Blend 3 for facilitating higher growth and titer.

6.4. Evaluation of Supplemented CDM

Three high performance supplement blends identified through statistical analysis were evaluated in larger-scale culture using two different CDM with two different CHO cell lines. Cell Line 1 was cultured in the 3 different media blends utilizing chemically-defined Media 1. Cell Line 2 was cultured in the 3 different media blends utilizing chemically-defined Media 2. A comparison of the culture conditions between these 2 sets of cultures is shown below in Table 3. An unsupplemented control was included for comparison purposes in both sets of experiments. Culture process conditions were similar to the 24-well plates used during the screening phase of the project, except the flask shaking/agitation speeds were decreased on a needed basis.

TABLE 3

Comparison Between Scale-Up Cultures Evaluating High Performance Supplemented CDM

| Process Condition | Cell Line 1 | Cell Line 2 |
|---|---|---|
| Initial viable cell density ($\times10^6$ cells/mL) | 0.4 | 0.4 |
| Culture Vessel | 125 mL Spinner | 500 mL Shaker |
| Working Volume (mL) | 75 | 150 |
| Basal Media | Media 1 | Media 2 |
| Temperature (° C.) | 35 | 35 |
| Agitation (rpm) | 70 | 140 |

6.5 Identification of Beneficial Supplements

The aforementioned supplements were evaluated for improvements in cell culture technique performance. The cell culture technique results were expressed relative to the control as per the below equations for each culture i:

$$\text{Peak } VCD \text{ Ratio} = \frac{\text{Peak } VCD_i}{\text{Peak } VCD_{control}} \quad \text{Eq. 1}$$

$$\text{Titer Ratio} = \frac{Titer_i}{Titer_{control}} \quad \text{Eq. 2}$$

The results from the screening studies are succinctly shown in FIG. 1. Each of the four quadrants in FIG. 1 represent distinct differences in cell culture technique performance depending on whether they increased or decreased VCD and titer relative to the average of the unsupplemented control. For better cell culture technique performance, the ideal cell culture technique media would support a higher peak viable cell density and higher harvest titer. Those conditions in the top right quadrant in FIG. 1 represent ideality. The largest increase in peak VCD from the screening experiments was 392%, whereas the largest increase in harvest titer was 205%. In general, no one supplement was able to account for these increases in process performance. The interaction of multiple supplements was required for this to be achieved. For any particular supplement, it is common to observe either a positive or negative relationship with the other supplements on the resulting process performance. Further analysis of these individual media compounds alone, and in concert with other compounds was utilized for the empirical determination of a high performance media supplement blend.

6.6. Univariate Inspectional Analysis

Table 4 highlights the ANOVA results for each of the respective supplements evaluated during the screening phase of the project.

TABLE 4

ANOVA Results from HTS Experiments

| Supplement(s) | Peak VCD p-value | Effect on Peak VCD | Harvest Titer p-value | Effect on Harvest Titer |
|---|---|---|---|---|
| Galactose + Sucrose + Sodium pyruvate | 0.58 | No change | 0.87 | No change |
| Trace metal mixture (TM) | 0.05 | No change | 0.07 | No change |
| Lipids mixture | 0.28 | No change | 0.46 | No change |
| NADH + NADPH | 0.91 | No change | 0.21 | No change |
| Inosine + Xanthine + Adenosine + Guanosine + Uridine + Cytidine | 0.00 | Decrease | 0.00 | Decrease |
| Concanavalin A | 0.00 | Decrease | 0.00 | Decrease |
| Polyamines mixture | 0.14 | Increase | 0.17 | Increase |
| Vitamin B-6 | 0.32 | No change | 0.12 | Increase |
| Vitamin B-12 | 0.49 | No change | 0.86 | Decrease |
| Essential amino acid mixture (EAA) | 0.01 | No change | 0.00 | Increase |
| Non-essential amino acid mixture (NEAA) | 0.06 | No change | 0.35 | No change |
| Mannose | 0.35 | Decrease | 0.03 | Increase |
| Fructose | 0.68 | No change | 0.96 | No change |
| Maltose | 0.75 | No change | 0.02 | Increase |
| Calcium pantothenate | 0.90 | Increase | 0.02 | No change |
| Putrescine | 0.00 | Decrease | 0.12 | No change |
| Cupric sulfate | 0.00 | Increase | 0.76 | Decrease |
| α-cyclodextrin | 0.06 | Increase | 0.11 | Increase |
| β-cyclodextrin | 0.02 | Increase | 0.67 | Increase |
| Taurine | 0.00 | Decrease | 0.02 | Decrease |
| Sarcosine | 0.78 | No change | 0.18 | Decrease |
| Ethanolamine | 0.03 | Increase | 0.23 | Decrease |
| Folate | 0.40 | Decrease | 0.11 | Decrease |
| Vitamins mixture | 0.01 | No change | 0.26 | No change |
| Nicotinamide | 0.38 | Decrease | 0.49 | No change |
| Cystine | 0.00 | Decrease | 0.00 | Decrease |
| Sodium selenite | 0.00 | Decrease | 0.00 | Decrease |
| Glutathione | 0.13 | Decrease | 0.59 | Decrease |
| Xylose | 0.46 | No change | 0.16 | Increase |
| GlcNAc | 0.99 | Decrease | 0.14 | No change |
| Arachidonic acid | 0.17 | Decrease | 0.89 | Decrease |
| Linolenic acid | 0.42 | Decrease | 0.65 | Decrease |
| Choline chloride | 0.05 | No change | 0.10 | No change |
| Iron supplement | 0.00 | Decrease | 0.00 | Decrease |
| Manganese chloride | 0.62 | Increase | 0.64 | No change |
| GalNAc | 0.91 | No change | 0.60 | Decrease |
| Linoleic acid | 0.06 | No change | 0.72 | Increase |
| PABA | 0.81 | Decrease | 0.05 | No change |
| Potassium phosphate | 0.00 | Increase | 0.00 | Decrease |
| EDTA | 0.08 | Increase | 0.00 | Decrease |
| Riboflavin | 0.07 | Decrease | 0.45 | No change |
| Biotin | 0.40 | No change | 0.89 | No change |
| Thymidine | 0.97 | No change | 0.04 | Decrease |
| Hydrocortisone | 0.25 | No change | 0.42 | Increase |
| L-alanyl-L-glutamine | 0.10 | Increase | 0.51 | No change |
| Sodium citrate | 0.48 | No change | 0.85 | No change |
| Sodium pyruvate | 0.00 | Decrease | 0.00 | No change |
| i-inositol | 0.98 | No change | 0.80 | No change |
| Zinc chloride | 0.69 | No change | 0.00 | Increase |

Figure 2:
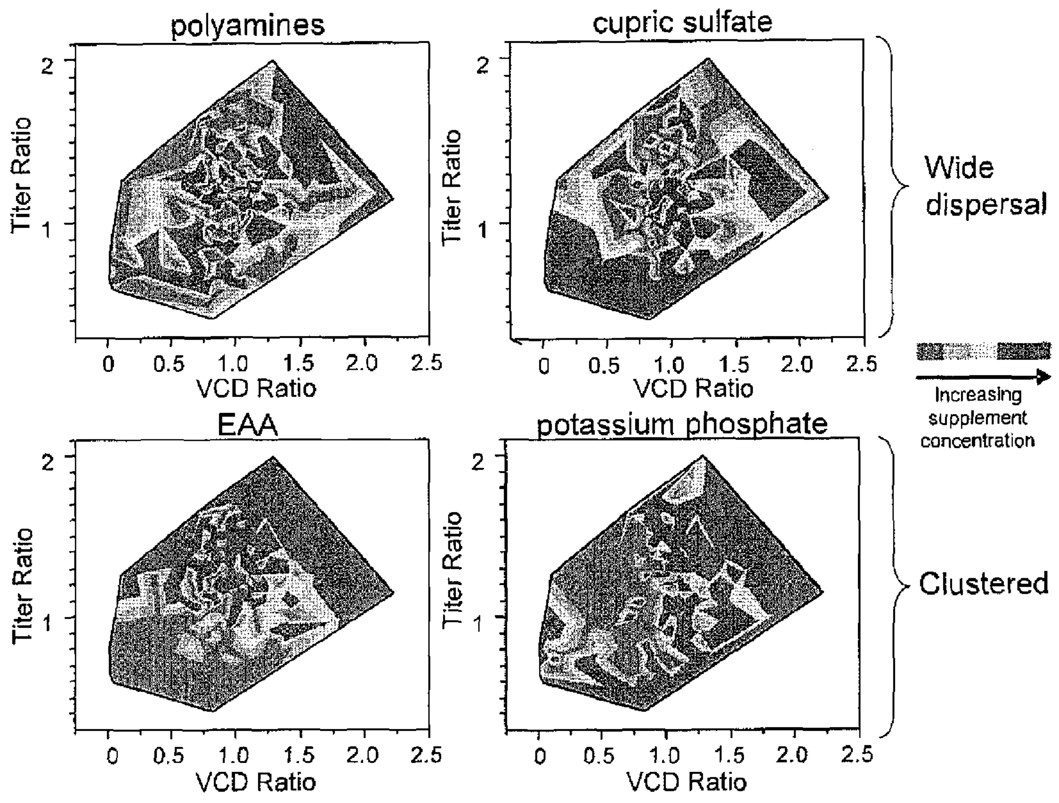
FIG. 2 depicts graphs of univariate data analysis on the process performance effect of individual supplements. In particular.

The data analysis of individual media components for their potential role in increasing process performance typically exhibited two distinct patterns: wide dispersal and clustered, as shown in FIG. 2. The supplements whose relative concentrations supported a distinct pattern of either increasing or decreasing process performance were categorized into the clustered classification. The supplements whose relative concentrations did not support any discernible pattern in either increasing or decreasing performance were categorized into the wide dispersal classification.

6.7. Multivariate Inspectional Analysis

Without being bound by any theory, it is believed that no individual media component can be utilized to increase cell culture technique performance across all different cell lines and chemically-defined media. Instead, the blending of compounds that by themselves are either obviously beneficial, marginally beneficial, or cause no performance increase at all, can synergistically interact to provide the culture environment for the cells to grow and secrete recombinant proteins in an higher-performing fashion. The present analysis takes a multi-dimensional perspective and obtaining a better understanding of how two or more media components interact to facilitate increased performance.

Figure 3:
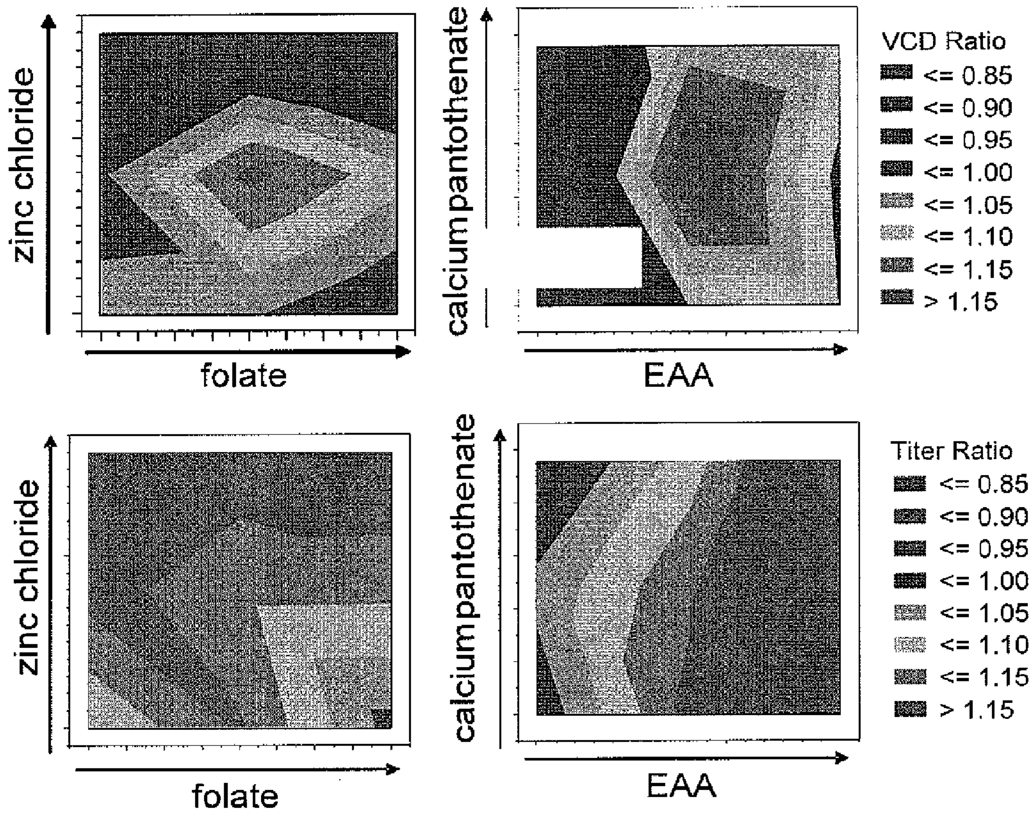
FIG. 3 depicts the interaction of multiple supplements at varying concentrations on process performance. In particular.

FIG. 3 highlights an example of this multi-dimensional perspective using zinc chloride and folate at varying concentrations. It is apparent that there is a range of zinc chloride and folate concentrations that supports an increase in viable cell density. However, this high performance blend does not necessarily support the highest titer ratio increase. This is commonly found within the screening studies dataset in that the supplement concentration ranges that support higher VCD and titer are not mutually exclusive. Without being bound by any theory, it is believed that there is a significant dependence of process performance increase on the levels of the essential amino acids. This multi-dimensional perspective towards cell culture technique media design is difficult when the number of media components being analyzed becomes large. For this, statistical software packages are useful so that an high performance blend based on the individual contributions of all components can be ascertained.

6.8. Identification of Beneficial Supplements and High Performance Supplement Blending Through either inspectional analysis, ANOVA results from the individual screening experiments, or use statistical software, a list of 23 supplements were determined to contribute positively towards an increased peak VCD and/or harvest titer. These supplements were either compounds or groups of similar compounds such as polyamines, essential amino acids, and vitamins. The listing of these beneficial media components is shown in Table 3.

TABLE 5

Supplements identified to increase cell culture technique performance

| | | |
|---|---|---|
| Polyamines mixture | Xylose | Mannose |
| Essential amino acid mixture (EAA) | Choline chloride | Ethanolamine |
| Maltose | Manganese chloride | Vitamins mixture |
| Calcium pantothenate | Potassium phosphate | Linoleic acid |
| Cupric sulfate | Thymidine | EDTA |
| α-cyclodextrin | i-inositol | Hydrocortisone |
| β-cyclodextrin | Zinc chloride | L-alanyl-L-glutamine |
| Folate | Pyridoxine hydrochloride | |

Fifteen of these supplements, or groups of supplements, were screened in a separate statistically designed experiment for the final determination of high performance media blends for the maximization of peak VCD, harvest titer, and both of these variables simultaneously. A comparison between the supplements in each of the three identified high performance media is shown below in Table 6.

TABLE 6

Process Performance Patterns Exhibited Through Media Supplementation

| Supplement | Process Performance Pattern |
|---|---|
| Polyamines mixture | Wide dispersal |
| Essential amino acid mixture (EAA) | Clustered |
| Maltose | Wide dispersal |
| Calcium pantothenate | Wide dispersal |
| Cupric sulfate | Wide dispersal |
| α-cyclodextrin | Wide dispersal |
| β-cyclodextrin | Wide dispersal |
| Folate | Wide dispersal |
| Xylose | Wide dispersal |
| Choline chloride | Wide dispersal |
| Manganese chloride | Wide dispersal |
| Potassium phosphate | Clustered |
| Thymidine | Wide dispersal |
| i-inositol | Wide dispersal |
| Zinc chloride | Clustered |

The JMP7 statistical software program was further used to identify the high performance media supplementation for maximizing peak VCD, harvest titer, and both simultaneously. A comparison between these high performance supplementation amounts is shown below in Table 7.

TABLE 7

Supplementation to Increase Cell Culture Performance

| Supplement | Concentration Target (Range) for Increase of Peak VCD (g/L)[a,b] | Concentration Target (Range) for Increase of Harvest Titer (g/L)[a,b] | Concentration Target (Range) for Increase of Peak VCD and Harvest Titer (g/L)[a,b] |
|---|---|---|---|
| Putrescine | 0 | $+1.20 \times 10^{-4}$ ( $1.06 \times 10^{-4}$-$1.36 \times 10^{-4}$) | $+1.20 \times 10^{-4}$ ($1.06 \times 10^{-4}$-$1.36 \times 10^{-4}$) |
| Spermine, free base | 0 | $+9.14 \times 10^{-5}$ ($8.11 \times 10^{-5}$-$1.04 \times 10^{-4}$) | $+9.14 \times 10^{-5}$ ($8.11 \times 10^{-5}$-$1.04 \times 10^{-4}$) |
| Spermidine, free base | 0 | $+4.76 \times 10^{-5}$ ($4.22 \times 10^{-5}$-$5.42 \times 10^{-5}$) | $+4.76 \times 10^{-5}$ ($4.22 \times 10^{-5}$-$5.42 \times 10^{-5}$) |
| Hypoxanthine | 0 | $+7.62 \times 10^{-4}$ ($6.76 \times 10^{-4}$-$8.68 \times 10^{-4}$) | $+7.62 \times 10^{-4}$ ($6.76 \times 10^{-4}$-$8.68 \times 10^{-4}$) |
| L-isoleucine | +0.26 (0.23-0.29) | +0.31 (0.27-0.35) | +0.31 (0.27-0.35) |
| L-leucine | +0.27 (0.24-0.31) | +0.33 (0.29-0.38) | +0.33 (0.29-0.38) |
| L-lysine | +0.41 (0.37-0.47) | +0.50 (0.44-0.57) | +0.50 (0.44-0.57) |
| L-methionine | +0.09 (0.08-0.10) | +0.11 (0.10-0.12) | +0.11 (0.10-0.12) |
| L-phenylalanine | +0.17 (0.15-0.19) | +0.20 (0.18-0.23) | +0.20 (0.18-0.23) |
| L-threonine | +0.23 (0.21-0.26) | +0.28 (0.25-0.32) | +0.28 (0.25-0.32) |
| L-tyrosine | +0.16 (0.15-0.19) | +0.20 (0.17-0.22) | +0.20 (0.17-0.22) |
| L-valine | +0.26 (0.23-0.30) | +0.32 (0.28-0.36) | +0.32 (0.28-0.36) |
| L-arginine | +0.60 (0.53-0.68) | +0.72 (0.64-0.82) | +0.72 (0.64-0.82) |

TABLE 7-continued

Supplementation to Increase Cell Culture Performance

| Supplement | Concentration Target (Range) for Increase of Peak VCD (g/L)[a,b] | Concentration Target (Range) for Increase of Harvest Titer (g/L)[a,b] | Concentration Target (Range) for Increase of Peak VCD and Harvest Titer (g/L)[a,b] |
|---|---|---|---|
| L-histidine*HCl*$H_2O$ | +0.21 (0.18-0.23) | +0.25 (0.22-0.28) | +0.25 (0.22-0.28) |
| L-tryptophan | +0.09 (0.08-0.10) | +0.10 (0.09-0.12) | +0.10 (0.09-0.12) |
| Maltose | 0 | +1.07 (0.95-1.21) | +1.07 (0.95-1.21) |
| Calcium pantothenate | +0.15 (0.13-0.17) | 0 | 0 |
| Cupric sulfate | +0.02 | 0 | 0 |
| α-cyclodextrin | +0.16 (0.14-0.18) | 0 | 0 |
| β-cyclodextrin | +0.16 (0.14-0.18) | 0 | 0 |
| Folate | +0.05 (0.05-0.06) | 0 | 0 |
| Xylose | 0 | +1.20 (1.06-1.37) | +1.20 (1.06-1.37) |
| Choline chloride | 0 | +0.78 (0.69-0.88) | +0.78 (0.69-0.88) |
| Manganese chloride | $+6.67 \times 10^{-5}$ ($5.91 \times 10^{-5}$-$7.59 \times 10^{-5}$) | $+1.07 \times 10^{-4}$ ($9.46 \times 10^{-5}$-$1.21 \times 10^{-4}$) | 0 |
| Potassium phosphate | +0.10 (0.09-0.12) | +0.09 (0.08-0.10) | +0.10 (0.09-0.12) |
| Thymidine | $+1.97 \times 10^{-3}$ ($1.75 \times 10^{-3}$-$2.25 \times 10^{-3}$) | 0 | 0 |
| i-inositol | +0.11 (0.09-0.12) | +0.05 (0.05-0.06) | +0.19 (0.17-0.22) |
| Zinc chloride | $+2.05 \times 10^{-3}$ ($1.82 \times 10^{-3}$-$2.33 \times 10^{-3}$) | $+5.46 \times 10^{-3}$ ($4.85 \times 10^{-3}$-$6.22 \times 10^{-3}$) | $+5.12 \times 10^{-3}$ ($4.54 \times 10^{-3}$-$5.83 \times 10^{-3}$) |

[a]Concentrations reflect the predicted amounts for addition into the unsupplemented control media for the corresponding high performance criteria
[b]Predicted concentrations subject to a range of potential values due to variability in culture volumes in the screening experiment utilized to identify these concentrations The above results indicate that there are some supplements that are unique for increasing peak viable cell density, and some that are unique for increasing harvest titer. Some supplements such as the essential amino acids, and zinc chloride are shared between increasing both peak VCD and titer either as separate criteria, or both criteria simultaneously. In the attempts to confirm that the supplement blends implicated through the screening studies did actually increase process performance, the respective concentrations of each of the supplements were scaled up to larger-scale assay.

Figure 4:
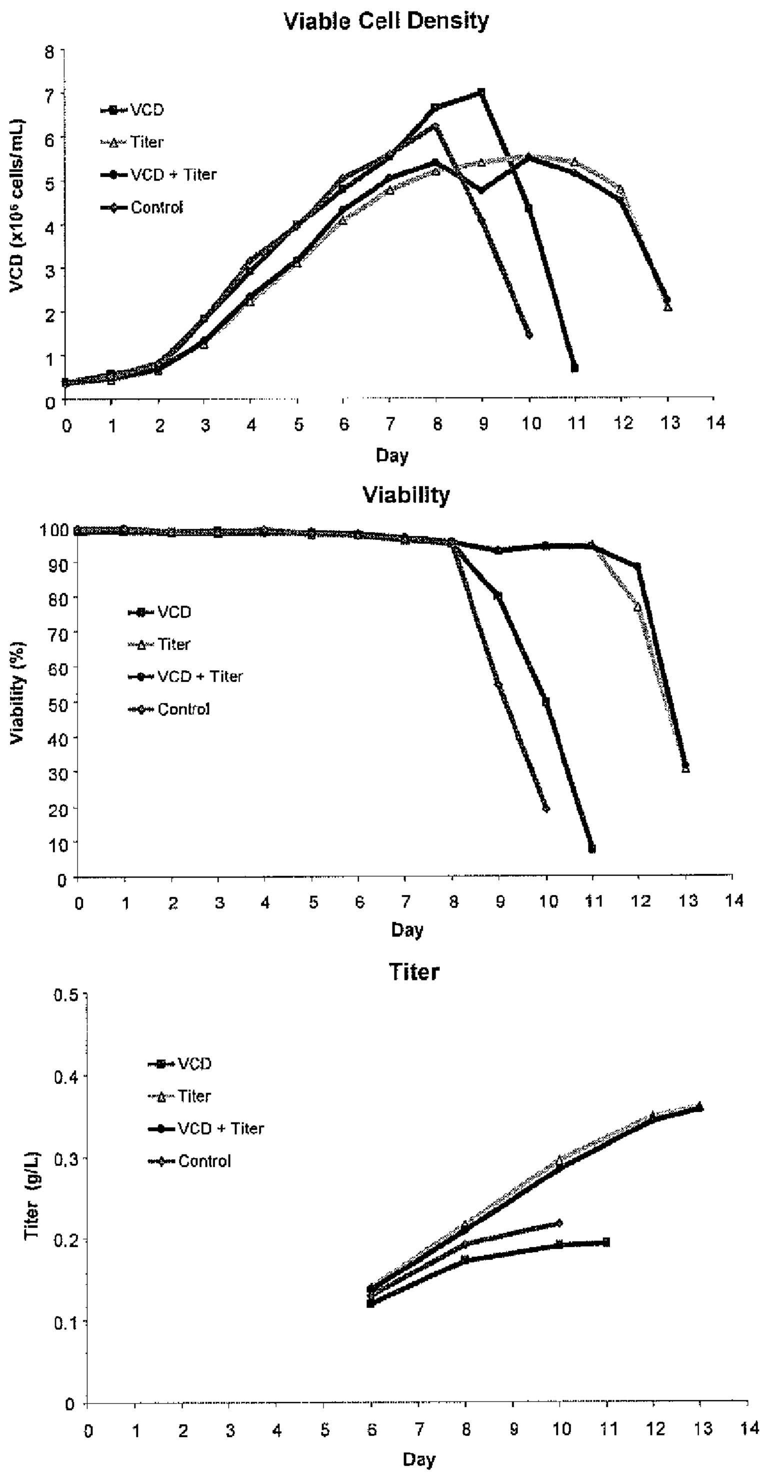
FIG. 4 depicts the process performance effects of three high performance supplemented media and one control on VCD, % viability, and titer.
Figure 5:
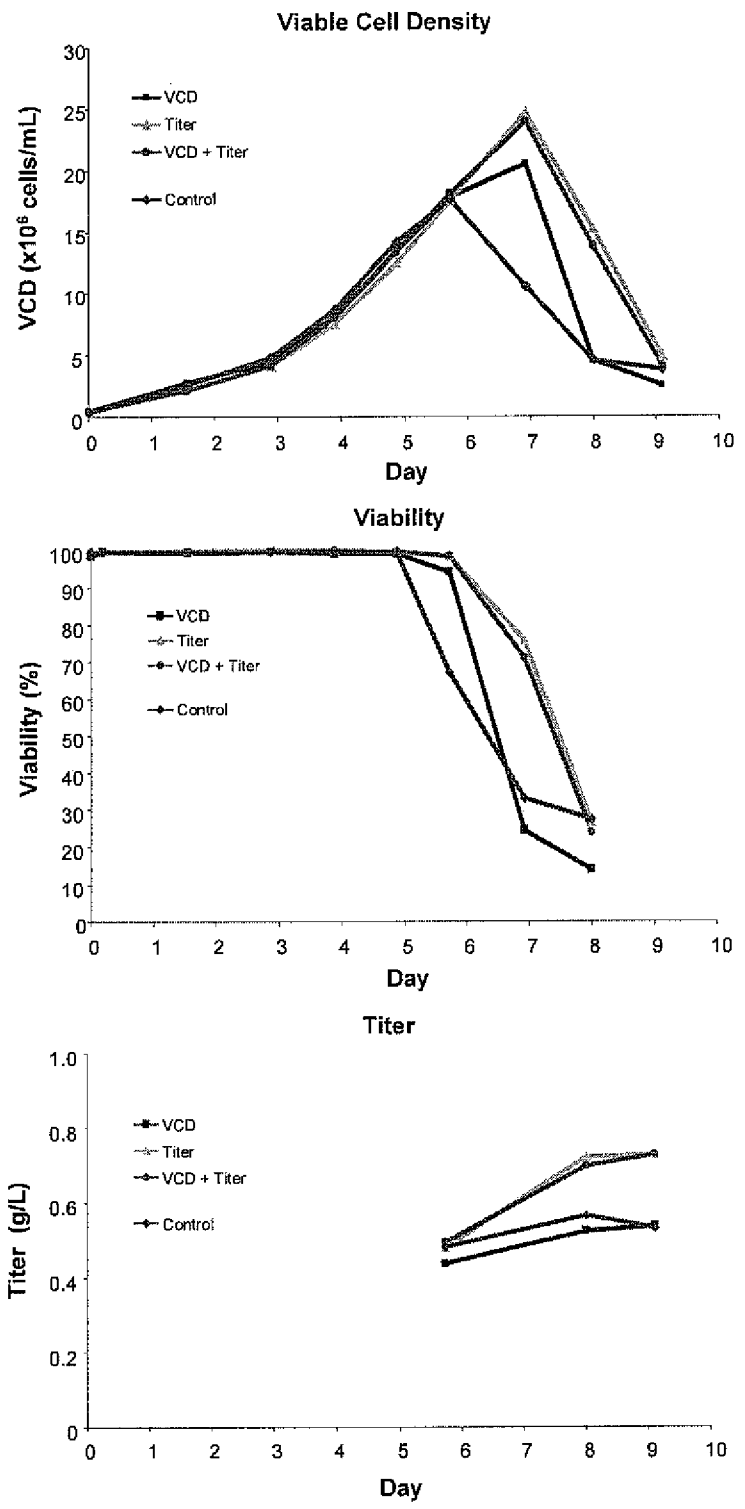
FIG. 5 depicts the process performance effects of three high performance supplemented media and one control on VCD, % viability, and titer.

6.9. Verification of Process Performance in High Performance Supplemented Chemically Defined Media Two separate cell lines cultured in two separate chemically defined medias were evaluated in scaled-up culture volumes to verify process performance improvements with high performance supplementation. Cell Line 1 was cultured in 125 mL spinner cultures using chemically-defined Media 1 as the growth media. Cell Line 2 was cultured in 500 mL shaker flask cultures using chemically-defined Media 2 as the growth media. In each scale-up experiment, the three high performance supplemented medias were evaluated. These experiments were designed to evaluate if an increase in process performance identified in one particular cell line and media, could carry over to other cells lines and media (i.e., that the identified beneficial supplement blending was not unique to either the cell or media). The cell culture results from these experiments are shown in FIGS. 4 and 5.

The results described herein indicate that the high performance supplemented media did behave as expected for both cell lines based on their selection criteria. The media identified as simultaneously high performance for VCD and titer facilitated a 12% decrease in peak VCD, and a 64% increase in harvest titer for Cell Line 1. This same media identified as simultaneously high performance for VCD and titer facilitated a 36% increase in peak VCD, and a 37% increase in harvest titer for Cell Line 2 in shaker flask culture. Interestingly, the collective results also suggest that the media identified for cell growth and titer behaved more similarly to the media identified for titer alone, which was consistent with their relative compositions in which there was more overlap between these two particular medias compared to the media identified for growth alone.

These results suggest that the identification of a particular high performance supplement blend in one particular mammalian cell line and chemically-defined media can cause a carry-over performance increase with a completely different cell line and media. Moreover, the high-throughput screening methods of the present invention have been able to successfully identify a high performance supplemented chemically defined media in an efficient and effective manner. The work required no costly capital infrastructure and was able to be completed on the time scale of months.

All patents, patent applications, publications, product descriptions and protocols, cited in this specification are hereby incorporated by reference in their entirety. In case of a conflict in terminology, the present disclosure controls.

While it will be apparent that the invention herein described is well calculated to achieve the benefits and advantages set forth above, the present invention is not to be limited in scope by the specific embodiments described herein. It will be appreciated that the invention is susceptible to modification, variation and change without departing from the spirit thereof.

What is claimed is:

1. A high-throughput method of screening cell culture media supplements to determine a concentration of a supplement combination capable of inducing an increase in peak viable cell density in a cell culture, the method comprising:

a. supplementing a plurality of individual volumes of chemically defined media with a supplement combination comprising L-isoleucine (0.23-0.29 g/L); L-leucine (0.24-0.31 g/L); L-lysine (0.47-0.37 g/L); L-methionine (0.08-0.10 g/L); L-phenylalanine (0.15-0.19 g/L); L-threonine (0.21-0.26 g/L); L-tyrosine (0.15-0.19 g/L); L-valine (0.23-0.30 g/L); L-arginine (0.53-0.68 g/L); L-histidine*HCl*$H_2O$ (0.18-0.23 g/L); L-tryptophan (0.08-0.10 g/L); Calcium pantothenate (0.13-0.17 g/L); Cupric sulfate (0.02 g/L); a-cyclodextrin (0.14-0.18 g/L); P-cyclodextrin (0.14-0.18 g/L); Folate (0.05-0.06 g/L); Manganese chloride ($5.91\times10^{-5}$-$7.59\times10^{-5}$ g/L); Potassium phosphate (0.09-0.12 g/L); Thymidine (1.75xle $2.25\times10^{-3}$ g/L); i-inositol (0.09-0.12 g/L); and Zinc chloride ($1.82\times10^{-3}$ $2.33\times10^{-3}$ g/L;

b. inoculating the individual volumes with a cell line of interest;

c. culturing the cell line of interest in the individual volumes;

d. measuring peak viable cell density of the cultured cell line in the individual volumes; and e. performing Analysis of Variance statistical analysis of the measurements of peak viable cell density;

wherein the results of the statistical analysis indicate the concentration of a supplement combination capable of inducing an increase in peak viable cell density in a cell culture.

2. The method of claim 1, wherein the cell line of interest is a prokaryote, yeast, or higher eukaryote cell line.

3. The method of claim 2, wherein the cell line is a mammalian cell line.

4. The method of claim 3, wherein the mammalian cell line is a Chinese Hamster Ovary cell line, a NS0 myeloma cell line, a COS cell line, a SP2 cell line, a monkey kidney CV1 cell line, a human embryonic kidney cell line, a baby hamster kidney cell line, a mouse sertoli cell line, an African green monkey kidney cell line; a human cervical carcinoma cell line, a canine kidney cell line, a buffalo rat liver cell line; a human lung cell line, a human liver cell line, a mouse mammary tumor cell line, a TRI cell line, a MRC 5 cell line, a FS4 cell line, or a human hepatoma cell line.

5. The method of claim 1, wherein the cell line of interest expresses a polypeptide of interest.

6. The method of claim 5, wherein the polypeptide of interest is an antibody.

* * * * *